United States Patent [19]

Hirsch et al.

[11] Patent Number: 5,053,429
[45] Date of Patent: Oct. 1, 1991

[54] TREATING INFLAMMATORY PAIN WITH METHIONINE

[75] Inventors: Gerald P. Hirsch, Atlanta, Ga.; Robert K. Bayless, Austin, Tex.

[73] Assignee: The Lithox Corporation, Inc., Austin, Tex.

[21] Appl. No.: 482,923

[22] Filed: Feb. 21, 1990

Related U.S. Application Data

[63] Continuation-in-part of Ser. No. 179,225, Apr. 8, 1988, abandoned.

[51] Int. Cl.$^5$ .......................................... A61K 31/195
[52] U.S. Cl. ................................................. 514/562
[58] Field of Search ....................................... 514/562

[56] References Cited

U.S. PATENT DOCUMENTS 3,952,115  4/1976  Damico et al. ..................... 426/615
4,315,028  2/1982  Scheinberg .......................... 424/290
4,711,780  12/1987  Fahim .................................. 514/562

FOREIGN PATENT DOCUMENTS 2821704  11/1978  Fed. Rep. of Germany .

OTHER PUBLICATIONS

Ambanelli, U., Sposni, A., Ferraccioli, G., Serum Antioxidant Activity and Related Variables, Scand. J. Rheumatology, 11: 203-207, 1982.
Bailey, K., Sheffner, A., The Reduction of Experimentally Induced Inflammation by Sulfhydryl Compounds, Biochemical Pharmacology, 16: 1175-1182, 1967.
Baldessarini, R., Stramentinoli, G., Lipinski, J., Methylation Hypothesis, Archives of General Psychiatry, 36: 303-307, 1979.
Banford, J., Brown, R., Hazelton, R., McNeil, C., Smith, W., Sturrock, R., Altered Thiol Status in Patients with Rheumatoid Arthritis, Rheumatology International, 2: 107-111, 1982.
Brattstrom, L., Israelsson, B., Jeppsson, J., Hultberg, B., Folic Acid—An Innocuous Mean to Reduce Plasma Homocysteine, Scand. J. Clin. Lab. Invest., 48: 215-221, 1988.
Bray, M., The Pharmacology and Pathophysiology of Leukotriene B4, Br. Medical Bulletin, 39: 249-254, 1983.
Cho, E., Andersen, B., Filer, L., Stegink, L., D-Methionine Utilization in Young Miniature Pigs, Adult Rabbits, and Adult Dogs, J. Parenteral and Enteral Nutrition, 4: 544-547, 1980.
Clark, R., Henson, R., Editors, The Molecular and Cellular Biology of Wound Repair, Plenum Press, New York, 1988, pp. 149-183.
Connor, H., Newton, D., Preston, R., Woods, H., Oral Methionine Loading as a Cause of Acute Serum Folate Deficiency: Its Relevance to Parenteral Nutrition, Postgraduate Medical J., 54: 318-320, 1978.
Cross, C., Halliwell, B., Borish, E., Pryor, W., Ames, B., Saul, R., McCord, J., Harman, D., Oxygen Radicals and Human Disease, Annals of Internal Medicine, 107: 526-545, 1987.
Cuperus, R., Muijsers, A., Wever, R., Antiarthritic Drugs Containing Thiol Groups Scavenge Hypochlorite and Inhibit Its Formation by Myeloperoxidase from Human Leukocytes, Arthritis and Rheumatism, 28: 1228-1233, 1985.
Davis, R., Inhibition of Inflammation with Certain Amino Acids, J. of the Am. Podiatry Assoc., 68: 24-30, 1978.
Delrieu, F., Ferrand, B., Amor, B., Etude Preliminaire de La L-Methionine dans le Traitement de La Polyarthrite Rhumatoide, Revue du Rhumatisme, 55: 995-997, 1988.
Eisenhauer, J., Gerald, M., The Nurse's 1984-1985 Guide to Drug Therapy, Prentice-Hall, New Jersey, 1984, pp. 246-266, and 584-602.
Fleisher, L., Gaull, G., Methionine Metabolism in Man: Developement and Deficiencies, Clinics in Endocrinology and Metabolism, 3:37-55, 1974.
Gatto, G., Caleri, D., Michelacci, S., Sicuteri, F., Analgesizing Effect of a Methyl Donor (S-Adenosylmethionine) in Migraine: An Open Clinical Trial, Int. J. Clin. Pharm. Research, 6: 15-17, 1986.
Gualano, M., Stramentinoli, G., Berti, F., Anti-Inflammatory Activity of S-Adenosyl-L-Methionine: Interference with the Eicosanoid System, Pharmacological Research Communications, 15: 683-696, 1983.
Hall, N., Blake, D., Bacon, P., Serum Sulphydryl Levels in Early Synovitis, J. of Rheumatology, 9: 593-596, 1982.
Inoue, Y., Zama, Y., Suzuki, M., D-Amino Acids as Immunosuppressive Agents, Japanese J. Exp. Medicine, 51: 363-366, 1981.
Johnson, J., Sustained Release Medications, Noyes Data Corp., New Jersey, 1980, p. 14.
Kies, C., Fox, H., Aprahamian, S., Comparative Value of L-, DL-, and D-Methionine Supplementation of an Oat-Based Diet for Humans, Jour. of Nutrition, 105: 809-814, 1975.
Leibovich, S., Ross, R., The Role of the Macrophage in Wound Repair, Am. J. of Pathology, 78: 71-91, 1975.
Malinow, M., Kang, S., Taylor, L., Wong, P., Coull, B., Inahara, T., Mukerjee, D., Sexton, G., Upson, B., Prevalence of Hyperhomocyst(e)inemia in Patients with Peripheral Arterial Occlusive Disease Circulation, 79: 1180-1188, 1989.
Marcolongo, R., Giordano, N., Colombo, B., Cherie--Ligniere, G., Todesco, S., Mazzi, A., Mattara, L., Leardini, G., Passeri, M., Cucinotta, D., Double-Blind Multicentre Study of the Activity of S-Adenosyl-Methionine in Hip and Knee Osteoarthritis, Current Therapeutic Research, 37: 82-84, 1985.
McKenna, F., Hickling, P., Kixon, J., Bird, H., Methylcysteine in Rheumatoid Arthritis, Br. J. of Rheumatology, 25: 132, 1986.
Montgomery, R., Dryer, R., Conway, T., Spector, A., Biochemistry a Case-Oriented Approach, Mosby Co., St. Louis, 4th Ed., 1983, pp. 466-470.
Olszewski, A., Szostak, W., Homocysteine Content of Plasma Proteins in Ischemic Heart Disease, Atherosclerosis, 69: 109-113, 1988.

Rao, A., Rao, S., Urinary Excretion of Taurine in Migraine Headache, 28: 133-4, 1988.

Remington's Pharmaceutical Sciences, Gennaro, A., Editor, Phil. College of Pharm. and Sci., 17th Edition, 1985, pp. 1585-1602.

Rotruck, J. Boggs, R., Comparative Metabolism of L-Methionine and N-Acetylated Derivatives of Methionine, J. Nutrition, 105: 331-7, 1975.

Rubin, R., Ordonez, L., Wurtman, R., Physiological Dependence of Brain Methionine and S-Adenosyl-Methionine Concentration on Serum Amino Acid Pattern, J. of Neurochemistry, 23: 227-231, 1974.

Sarwar, G., Peace, R., Comparisons Between True Digestibility of Total Nitrogen and Limiting Amino Acids in Vegetable Proteins Fed to Rats, Jour. of Nutrition, 116: 1172-1184, 1986.

Selmaj, K., de Belleroche, J., Das, I., Rose, F., Leukotriene B4 Generation by Polymorhonuclear Leukocytes: Possible Involvement in the Pathogenesis of Headache, Headache, 26: 460-464, 1986.

Simpson, D., Ross., The Neutrophilic Leukocyte in Wound Repair, J. of Clinical Investigation, 51: 2009-2023, 1972.

Spector, W., An Introduction of General Pathology, 2nd Edition, Churchill Livingstone, New York, 1980, pp. 58-75.

Stegink, L., Bell, E., Filer, L., Siegler, E., Andersen, D., Seligson, F., Effects of Equimolar Doses of L-Methionine, D-Methionine and L-Dethionine-dl-Sulfoxide on Plasma and Urinary Amino Acids Levels in Normal Adult Humans, J. Nutrition, 116: 1185-1192, 1986.

Stegink, L., Filer, L., Baker, G., Plasma Methionine Levels in Normal Adult Subjects after Oral Loading with L-Methionine and N-Acetyl-L-Methionine, J. Nutrition, 110: 42-49, 1980.

Stendahl, O., Coble, B., Dahlgren, C., Hed, J., Molin, L., Myeloperoxidase Modulates the Phagocytic Activity of Polymorphonuclear Neutrophil Leukocytes. Studies with Cells from a Myeloperoxidase-Deficient Patient, J. Clinical Investigation, 73: 366-373, 1984.

Stramentinoli, G., Pharmacologic Aspects of S-Adenosylmethioine, Am. J. of Medicine, 83(Suppl. 5A): 35-42, 1987.

Tsan, M., Chem, J., Oxidation of Methionine by Human Polymorphonuclear Leukocytes, J. Clinical Invest., 65: 1041-50, 1980.

Weissmann, G., Smolen, J., Hoffstein, S., Polymorphonuclear Leukocytes as Secretory Organs of Inflammation, J. of Investigative Dermatology, 71: 95-99, 1978.

Williamson, M., Fromm, H., The Incorporation of Sulfur Amino Acids into the Proteins of Regenerating Wound Tissue, J. of Biological Chemistry, 212: 705-712, 1955.

Dermatologic Clinics, 4: 127-136, 1986.

*Primary Examiner*—Stanley Friedman

[57] ABSTRACT

This invention concerns novel methods employing compositions containing as an active antioxidant or antiinflammatory agent the amino acid methionine, and/or one or more related compounds including certain metabolic precursor compounds, for treating or inhibiting inflammation and inflammatory pain in a subject. The compounds include the methionine hydroxy analogs, as well as compounds having the structural formula I:

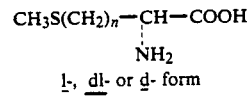

$$CH_3S(CH_2)_n-CH-COOH$$
$$|$$
$$NH_2$$

l-, dl- or d- form and pharmaceutically acceptable N-(mono- and di-carboxylic acid) acyl derivatives and alkyl esters thereof, where n is an integer from 1 to 3.

8 Claims, No Drawings

TREATING INFLAMMATORY PAIN WITH METHIONINE

This application is a continuation-in-part of application Ser. No. 07/179,225, filed on Apr. 8, 1988, now abandoned.

TECHNICAL FIELD

This invention concerns novel methods employing antiinflammatory compositions containing the amino acid methionine (also known as "Met"), and/or one or more related compounds including certain metabolic precursor compounds for treating inflammation and inflammatory pain in animals and man, and for the prevention of inflammation and inflammatory pain in animals and man, exemplified by recurrent headache pain, joint pain, wound pain, and the like.

BACKGROUND OF THE INVENTION

A variety of efforts have been made over many years to elucidate the mechanisms and origins of various forms of arthritis and headache. Limited success has been achieved in alleviating the symptoms of these diseases. Antioxidant therapy has been recommended as one method to alleviate the damage inflammation causes (Cross, et. al., Annals of Internal Medicine, 107:526-45, 1987).

Arthritis

Recently, several investigators have focused on the role of sulfhydryl compounds in the mechanism of treatment of some forms of arthritis. Cuperus, (Arthritis and Rheumatism 28: 1228-33, 1985) showed that d-penicillamine, tiopronin, aurothiomalate and aurothioglucose were scavengers of the products of activated granulocytes, and Bailey and Sheffner (Biochemical Pharmacology 16: 1175-82, 1967) showed that acetylcysteine and acetylpenicillamine reduced experimental dermal inflammation but that methionine did not. Methionine is known to be oxidized to its sulfoxide by granulocytes but not by hydrogen peroxide at physiological concentrations. Persons deficient in the enzyme myeloperoxidase do not make hypocholorous acid in lymphocytes and appear not to suffer unusually from infections. By contrast, persons with deficient production of hydrogen peroxide are adversely affected. (Stendahl, et al., J. Clin. Invest., 73:366-73, 1984).

Cuperus, supra, describes a feature of inflamed synovial fluid, such as that occurring in arthritis patients, as the accumulation of polymorphonuclear (PMN) leukocytes. One function of the leukocytes is the destruction of invading elements such as microorganisms. For this destruction, the leukocyte releases hydrogen peroxide and enzymes, e.g., myeloperoxidase, into the extracellular fluid. In the presence of hydrogen peroxide and chloride ion, myeloperoxidase catalyzes the formation of reactive hypochlorous acid (HOCl) which can oxidize tissue components and plasma protease inhibitors. Oxidation and subsequent inactivation of these protease inhibitors in vivo may lead to unrestrained proteolysis, resulting in severe tissue damage. (Weissmann, et. al., Jour. Investigative Dermatology, 71:95-9, 1978).

Several investigators have noted that patients with severe rheumatoid arthritis have lower levels of serum SH groups (Hall, Journal of Rheumatology 9:593-6, 1982; and Banford, et. al., Rheumatology, Int., 2: 107-11, 1982). Ambanelli (Scand. Jour. Rheumatology 11:203-7, 1982) showed that serum SH groups went up in patients that responded to tiopronin therapy. The mechanism of serum SH groups in relation to the severity of arthritis has not been established. The correlation could be explained by the failure of particular individuals to counteract the production of oxidizing substances by immunocytes.

McKenna, (British J. Rheumatology 25:132, 1986), saw benefit for only 2 of 15 patients given cysteine methyl ester for rheumatoid arthritis, a direct sulfhydryl agent.

Delrieu, et al., (Revue du Rhumatisme, 55:995-7, December, 1988) found no statisical difference between treatment and controls in a 24 patient study of rheumatoid arthritis using 5 and 10 grams of l-methionine per day for 4 and 2 months, respectively. Clinical tolerance was good, but gastrointestinal distress was encountered by a majority of the patients.

Gualano (Pharmacology Research Comm., 15:683-96, 1983) showed antiinflammatory activity of S-adenosyl methionine but attributed its effects to mechanisms of aspirin-like drugs. Davis, (Jour. Am. Pod. Assoc. 68:24-30, 1978) studied the effects of certain amino acids on inflammation measured as edema and found that methionine was not effective in reducing edema while cystine was effective. Marcolongo (Current Therapeutic Research 37:82-94, 1985) showed beneficial effects of S-adenosyl methionine slightly better than ibuprofen in the treatment of hip and knee osteoarthritis. Stramentinoli (Am. Jour. Medicine, 83 Suppl 5A:35-42, 1987) shows that S-adenosyl methionine will inhibit the swelling in carrageenin-induced rat paw edema, while l-methionine in equimolar doses is completely ineffective. Other studies involving the oral administration of S-adenosyl methionine have shown that treatment does not increase the blood levels of methionine (Baldessarini, et. al., Arch. Gen. Psychiatry, 36:303-7, 1979).

In a study of the immunosuppressive activity of D-amino acids, Inoue, et al. showed that there was no immunosuppressive effect for d-methionine in their mouse assay at a dose of 10 mg per kg body weight. (Japanese J. Experimental Medicine, 51:363-6, 1981).

Wound Healing

Wounds, whether accidental or surgical, can be the site of acute pain during the healing process. The macrophage, but not the neutrophil, is essential to the wound repair process. (Leibovich and Ross, Am. Jour. Pathology, 78:71-91, 1975; and Simpson and Ross, Jour. Clinical Invest., 51:2009-23, 1972). The release of toxic oxygen metabolites and proteolytic enzymes by PMNs may potentiate tissue injury and prolong inflammation (The Molecular and Cellular Biology of Wound Repair, Clark and Henson, Eds., Plenum Press, New York, 1988, p.149-83). Methionine is incorporated into regenerating wound tissue, and a steady supply is necessary for proper healing. (Williamson and Fromm, Jour. Biological Chemistry, 212:705-12, 1955). If the inflammatory contribution of the PMN could be reduced, while bacterial contamination is controlled by antibiotics, the pain associated with wound repair could be ameliorated.

Migraine

Selmaj, et al. (Headache 26: 460-464, 1986) have shown that plasma leukotriene B4 is elevated in patients with cluster headaches during the headache but not during cluster-headache-free periods while by contrast, some migraine patients had elevated leukotriene B4 levels during and between migraine headaches. Leukotriene B4 is a product of polymorphonuclear and other cells and has a number of stimulating effects on polymorphonuclear cells including chemokinesis, chemotaxis, aggregration, degranulation, and adherence (Bray, Brit. Med. Bulletin 39: 249-254, 1983).

The long term administration of S-adenosyl l-methionine (a single 400 mg injection per day) reduced the intensity, frequency and duration of migraine headaches. The mechanism of action is thought to be on 5-hydroxytryptamine turnover (Gatto, et. al., Int. J. Clin. Pharm. Res. 6:15-7, 1986). Other studies involving the oral administration of S-adenosyl methionine have shown that treatment does not increase the blood levels of methionine (Baldessarini, et. al., Arch. Gen. Psychiatry, 36:303-7, 1979). In animal studies blood level increases of methionine are reflected by parallel increases in brain levels of methionine, but a 10 fold increase in brain methionine produces only a 50% increase in brain S-adenosyl methionine (Rubin, et al., J. Neurochemistry 23: 227-231, 1974).

Decreased urinary excretion of taurine has been noted for migraine sufferers. Migraineurs have urinary taurine levels only half that of normal persons. The mechanism to account for this difference is unknown and the relationship of this observation to the occurance of migraine headaches is uncertain (Rao and Rao, Headache 28: 133-4, 1988).

Regarding acute inflammation, the complement system of the human body (see Spector, W. G., Intro. to General Pathology, p. 58-75, Churchill Livingstone, New York, 1980) is part of a cascade of enzyme reactions that are responsive to external injury in which complement is activated and generates peptides known as C3a and C5a which are response-inducing or chemotactic for white The S-methyl derivative of methionine, S-methyl methionine, also known as vitamin U has been shown to have benefit as an anti-ulcer compound and to have benefit for allergies. The same benefit is shown for carboxyl esters and N-acyl derivatives (Kowa, DT 2821-704). However, in this teaching no distinction is made for the d- and l- isomers of S-methyl methionine or its derivatives and no claim is made that these compounds act through anti-inflammatory mechanisms.

Dietary Deficiency of Methionine

Methionine deficiency is not recognized as a disease state in modern countries where adequate total protein is generally available. While it is recognized that humans, in contrast to most other mammals, cannot utilize d-methionine as a source of methionine, it is generally assumed that humans can utilized methionine sulfoxide as a source of methionine. The only suggestion that methionine sulfoxide might not be nutritionally equivalent to methionine is the lack of increase of blood l-methionine after adminstration of l-methionine sulfoxide. Humans enzymes have been found that can reduce methionine sulfoxide to methionine.

Methionine is known to be affected by a variety of food processing activities. l-Methionine is converted to d-Methionine when proteins are heated and a significant amount of the nutritional value of methionine can be lost by this mechanism. However, most of the potential loss of available methionine occurs through the mechanism of oxidation of methionine to methionine sulfoxide. The bleaching of flour is the major cause, when during the process of bleaching the chlorine is able to react with methionine. When proteins are heated with reducing sugars methionine is readily oxidized so that items such as canned peaches are potential sources of food with a deficiency of available methionine. More recently, as unsaturated fats replace saturated fats in prepared food sources additional sources of methionine oxidation occur. For example, the unsaturated fats in cake mixes held in a hot warehouse would result in oxidation of methionine to its sulfoxide. Published evidence for an extensive loss of methionine in food processing as regards human nutrition occured in the manufacture of instant oatmeal where the product used in nitrogen balance studies apparently had no nutritionally available methionine (see Kies, et. al., J. Nutrition, 105: 809-14, 1975). In the cooking of several types of beans 40% to 50% of the methionine is not available to rats (Sawar and Peace, J. Nutrition, 116:1172-84, 1986). The dietary requirement for methionine plus cysteine is based on nitrogen balance studies where a total of 800 mg per day is required to bring 50% of adults into positive nitrogen balance. No attempt has been made to determine the level of methionine that might be optimal for the prevention of oxidative damage.

Discussion

Methionine has been shown to be a target for the products of stimulated polymorphonuclear neutrophils (Tsan and Chen, J. Clin. Invest., 65:1041-50, 1980). The granular fraction of the PMNs oxidizes methionine to its sulfoxide in the presence of peroxide. Peroxide does not oxidize methionine to its sulfoxide at normal physiological concentrations.

Some of the differences measured in the relative effectiveness of methionine compounds and other chemicals especially in sulfhydryl reducing substances may be attributed to the control mechanisms that operate in animals and man to regulate the amounts of these substances wherein giving more of a substance does not significantly increase blood and tissue levels of that substance. Stegink, (Jour. Nutrition, 116:1185-92, 1986), showed that 0.5 gm of methionine elevated total blood methionine 2-fold for 2 hours with l-methionine but 3-fold for 4 hours with d-methionine. In the same study it was shown that methionine sulfoxide administration did not result in elevation of blood methionine. This observation suggests that methionine sulfoxide is not readily reduced to methionine but it is possible that this reduction occurs in tissues where the methionine remains sequestered. l-Methionine is an essential amino acid for human nutrition. The normal serum level of methionine in man is 15 ppm. dl-Methionine is available as a one-a-day food supplement in 500 mg. oral tablet form.

Regarding human nutrition, l-methionine is an essential amino acid whereas d-methionine is non-nutritive. For purposes of metabolism, l-methionine via S-adenosylmethionine has an important methylating function. In this function it loses a methyl group from its sulfur atom to become homocysteine. Homocysteine, as is known, when in excess can lead to homocysteinuria, and may be heart disease associated (Malinow, et al., Circulation 79:1180-88, 1989) and (Olszewski and Szostak, Atherosclerosis 69:109-13, 1988). Folic acid has been shown to be an innocuous method to reduce plasma homocysteine levels (Brattstrom et al., Scand. J.

Clin. Lab. Invest. 48:215-221, 1988). Administration of 8 grams of l-methionine to adult subjects for four days caused a greater than 30% reduction in serum folate levels (Conner, et al., PostGrad. Med. J. 54:318-20, 1978). Thus, folate should be co-administered whenever methionine is chronically consumed.

Administration of large amounts (5 to 10 grams per day) of l-methionine can cause gastrointestinal upset. Many people report a burning sensation in the stomach after taking methionine, along with an upset stomach and flatulance (Delrieu, et al, Revue du Rhumatisme, 55: 995-7, 1988). Enteric coating and timed-release formulations should avoid the stomach problems and allow even elevations of blood methionine for maximum anti-oxidant effect. Typical enteric coating agents include cellulose acetate phthalate, and other cellulose ethers and derivatives (Johnson, J. C., in Sustained Release Medications, Noyes Data Corp, New Jersey, 1980, p.14).

The Food and Nutrition Board of the U.S. National Academy of Sciences has established the Recommended Daily Allowance (RDA) for nutrients for most healthy individuals. For a discussion, see The Nurses Guide to Drug Therapy, Eisenhauer and Gerald, Prentice-Hall, New Jersey, 1984-5, pages 584-602, and incorporated here by reference. RDA's include: Vitamin B12: 3 mcg.; Vitamin B6: 2 mg; Folic Acid, 400 micrograms.

Different species utilize d-forms of amino acids to different extents. Humans and monkeys utilize d-methionine poorly while pigs, dogs, rabbits, chickens, rats and mice use d-methionine as a sulfur source fairly well. Animals do not metabolize N-blocked-d-methionine as they do N-blocked-l-methionine. Some N-blocking groups are not cleaved by enzymes that remove common blocking groups such as acetyl groups (Cho, Jour. Parenteral and Enteral Nutrition 4: 544-7, 1980; Stegink, Jour. of Nutrition 110: 42-9, 1980; Rotruck, Jour. of Nutrition 105: 331-7, 1975).

The patent to Scheinberg U.S. Pat. No. 4,315,028 describes a method of treatment of arthritis employing substituted cysteines.

The patent to Kowa (DT 2821-704) describes antiulcer activity and antiallergy benefits for the S-methyl derivative of methionine and methionine esters and N-acyl derivatives. The d-and l- isomers of S-methyl methionine compounds and derivatives are not distinguished.

The patent to Damico U.S. Pat. No. 3,952,115 describes foodstuffs containing N-acyl l-methionine esters and N-acyl l-cysteine esters. d-Isomers are specifically excluded because they are "not nutritionally available".

The patent to Fahim, U.S. Pat. No. 4,711,780, shows the benefit of the combination of cysteine with vitamin C and zinc salts in a topical mixture for stimulating cell proliferation. The benefit of methionine is claimed but not shown. No demonstration of benefit or claim for systemic administration is made.

There is a need at present for means of treating disease conditions of the kind in which a nutritional deficiency, a pain response or abnormal imflammatory pain is implicated.

It is therefore an object of the present invention to provide methods for the prevention and treatment of disease conditions of man and animals that may be attributable to or result from nutritional deficiency, inflammatory responses, or abnormal inflammation.

It is a further object of the invention to provide means for preventing or alleviating symptoms of homocysteinuria that may result from excess methionine intake.

These and other objects, features and advantages will be seen from the following detailed description of the invention.

SUMMARY AND DETAILED DESCRIPTION OF THE INVENTION

Our invention is based on the discovery that certain methionine or methionine-type compounds in the dl-form or d-form at relatively high, well-tolerated doses are potent antioxidant and antiinflammatory agents in man and animals. The compounds are especially important when administered or used for treatment in dosage form, for relieving, inhibiting or abolishing any of various inflammatory disease conditions or syndromes, e.g., conditions or syndromes presenting as inflammatory pain, post-surgical pain, joint pain, sports medicine pain, recurrent headache pain, wound healing inflammation, and the like. The methionine compounds in high daily dosage according to the invention thus may act in vivo to inhibit oxidative effects such as the action of hypochlorous acid to produce proteolysis and tissue damage.

The inclusion of vitamins B6, B12 and folate and the amino acids glycine and serine for homocysteine normalization are also disclosed.

For purposes of the invention, one uses at least one methionine-type compound selected from the methionine hydroxy analogs and methionine compounds having the structural formula I

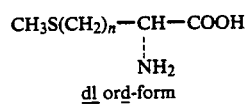

dl ord-form and pharmaceutically acceptable N-(mono- and di- carboxylic acid) acyl derivatives of methionine compounds and alkyl esters of methionine and analog compounds, where n is an integer from 1 to 3.

Thus, the methionine-type compound (for convenience sometimes referred to herein as "methionine" or "methionine compound") may be normethionine (n=1), methionine (n=2), homomethionine (n=3), the hydroxy analog, or the acyl or alkyl ester derivatives thereof, as defined. Exemplary acyl derivatives are the formyl, acetyl, propionyl, and succinyl derivatives, of which the formamide, acetamide and succinyl derivatives are preferred. Exemplary ester derivatives are methyl, ethyl and isopropyl esters.

The mechanism underlying the present invention is believed to be that the methionine compound acts in vivo to reduce the effect of release by polymorphonuclear leukocytes (PMNs) of hypochlorous acid and other oxidants so that systemic oxidation, proteolysis, and tissue damage are inhibited. It is believed that the l-form of the methionine compound serves to fulfill its essential, recognized nutritional need whereas it is the d-form that has a previously unrecognized potent and different action at high dosage which is a well tolerated antiinflammatory activity.

In trials where the antioxidant activity was compared with that of ascorbic acid (a known antioxidant substance), methionine, methionine sulfoxide, S-Methyl cysteine, and vitamin U (S-Methyl methionine), were mixed with an equimolar amount of vitamin C (ascorbic acid) and then titrated with sodium hypochlorite. Methionine was three times better (equimolar basis) than vitamin C as an antioxidant for HOCl. S-Methyl cysteine had about the same level of antioxidant activity as methionine. Methionine sulfoxide and vitamin U did not affect the oxidation of vitamin C by sodium hypochlorite (as measured by the decrease in ultraviolet absorption at 270 nanometers). Thus, neither S-methyl methionine nor methionine sulfoxide are suitable for reducing the effect of hypochlorous acid produced by PMNs (neutrophils).

In contrast to vitamin C which has limited oral uptake of about 100 mg per day methionine can be elevated to quite high levels (up to 25 times normal levels) in the body by administration of methionine. Spaced administration of 1.5 grams of d-methionine results in a 3 fold increase in blood levels of methionine. Because d-methionine has a much longer half-life than l-methionine and because d-methionine is transported into the brain while most other d-amino acids to not penetrate the blood-brain barrier, it is anticipated that when dl- or d-methionine is administered with other dietary antioxidants a synergistic effect of overall antioxidant effect will be seen. Synergistic antioxidant effects can be detected in humans with arthritis by measuring the reduction of blood levels of mixed cysteine/homocysteine disulfides.

The method for treating inflammation or pain in a subject may also employ administering in the dosage form with the methionine compounds at least one homocysteine reducing or remethylating compound sometimes referred to herein as a homocysteine affecting compound. The homocysteine affecting compound is at least one homocysteine affecting amino acid or homocysteine affecting vitamin selected from the group consisting of glycine, serine, vitamin B12, vitamin B6, and folic acid or folate, the compound being present in an amount sufficient to enable the systemic conversion of homocysteine to methionine or cysteine. The metabolic pathways for such conversion are detailed in: Biochemistry—A Case Oriented Approach, Montgomery, Dryer, Conway, Spector, eds., Mosby Co., London, IV Ed., 1983, p. 466–70; and: Fleisher and Gaull, Clinics in Endocrinology and Metabolism, 3:37–55, 1974; incorporated herewith by reference. Background for this is that methionine may have an adverse effect when given to subjects with vitamin B12 or folate deficiency. This effect is thought to be due to a buildup of systemic homocysteine; homocysteine is poorly remethylated in the absence or deficiency of vitamin B12 or folate. Also, the vitamin B6 level may be too low for the metabolism of homocysteine to cysteine by way of cystathionine. Thus, chronic comsumption of excess dl-methionine, for example, may result in mild homocysteine elevation unless other co-factor substances are used or supplemented to stimulate the transformation of the excess homocysteine. The buildup is avoided, according to the invention, by including at least one homocysteine affecting compound in the dosage: vitamin B12 and folate to insure that homocysteine can be systemically remethylated to methionine; glycine or serine to insure that homocysteine can be reduced by way of cystathionine to cysteine; and vitamin B6 to insure that homocysteine can be metabolized to cysteine. The amino acids glycine and serine preferably are present in the serving or dosage in an amount from 1/5 to 3 times the amount of methionine compound The nutrients, vitamins B12, B6 or folate preferably are present in the total daily dosage range of: B12, 0.3 to 30 micrograms; B6, 0.2 to 20 milligrams; folate, 40 to 4000 micrograms; and combinations thereof.

To the extent that conditions benefited by the consumption of dl-methionine are the result of a dietary deficiency of l-methionine it may be desirable to replenish methionine in food products as is currently done for a number of vitamins that are also made unavailable by food processing. The invention also concerns methods for providing methionine in the final product for consumption in the amount that provides for replacement of unavailable methionine and additional methionine that would accomplish the teachings herein where it is desirable to obtain the additional antioxidant amount in a normal food item.

It is found according to the invention that methionine, by its systemic antioxidant effect, especially d-methionine in humans  d N-acetyl d-methionine in animals, systemical  e activity of immunocytes, especiall.  nuclear neutrophils (PMNs).

The best method to practice the teachings of described compounds depends on the particular conditions being treated and the compositions that are required to produce optimal results. Glycine and serine are needed to prevent abnormal homocysteine levels which otherwise would occur when compounds containing dl-methionine or its derivatives are consumed. In those cases where the methionine compound is dl-methionine or a derivative of dl-methionine the inclusion of homocysteine affecting amino acids and homocysteine affecting vitamins assures adequate conversion of homocysteine to cysteine or the methylation of homocysteine to methionine. When methionine compounds are used in the upper portion of the dosage range dissolution of the compound in the stomach should be slowed. Also, individuals that are more sensitive to gastric upset should be provided with slow dissolving compositions to get effective relief.

Inflammatory Pain

In one preferred embodiment, the invention concerns a method to treat inflammation or pain in a subject, such as inflammatory pain, joint pain, wound pain, post-surgical pain, recurrant headache pain, sports medicine pain, and the like. The method comprises administering to the subject in dosage form an effective inflammation or pain relieving amount of at least one methionine compound as defined above.

In another aspect, the method employs an analgesic composition in dosage form comprising at least one methionine compound as defined above and at least one art-recognized analgesic or anti-inflammatory substance that is compatible and preferably effective in oral dosage form (as detailed, e.g., in The Nurses's Guide to Drug Therapy, op.cit., p. 246–66, incorporated herewith by reference). Among such substances may be mentioned:

Aspirin
carbaspirin
choline salicylate
diflunisal
magnesium salicylate
salicylamide
salicylic acid
salsalate
sodium thiosalicylate acetaminophen
phenacetin
aminopyrine
mefenamic acid
methotrimeprazine
oxyphenbutazone
phenylbutazone
indomethacin
ibuprofen
sulindac
piroxicam
meclofenamate
zomepirac
codeine
morphine
meperidine
pethinine
alphaprodine
fentanyl
levorphanol
methadone
phenazocine
butorphanol
ethobeptozine
nalbuphine
pentazocine
propoxyphene
fenoprofen
naproxen
tolmeton
and the like. Because the mechanism of action of methionine is different from the mechanism of action of these art recognized compounds, a synergistic anti-inflammatory or analgesic effect can according to the invention be expected.

For this purpose, the analgesic substance and the methionine compound are present in an appropriate pharmaceutical dosage form, preferably in a sustained release or controlled release form (e.g. an enteric coated or slow release form, which may be per se conventional), to enhance or ensure release in the intestine rather than the stomach, optionally with suitable excipients, such that each substance contributes its respective analgesic and/or anti-inflammatory effect when a unit dosage of the composition is administered. A preferred composition for human use is one where the unit dosage of the methionine compound, preferably dl-methionine, is sufficient to provide a total daily dosage range of about 1.0 to 10 gm/70 kg of body weight.

One person, who was taking three to four 400 mg tablets of ibuprofen per day for pain from a shoulder injury was able to reduce his intake to one tablet per day while consuming two 500 mg tablets of dl-methionine per day.

A preferred treatment regimen is a daily oral dose of 1.5 to 3 gm/70 kg. of body weight taken in spaced, preferably mealtime, doses.

Another preferred treatment regimen employs dl-methionine in the dosage range of 0.5 grams to 3 grams per day and the analgesic asprin (acetylsalicilic acid) in the amount of 325 mg per 0.5 gram of methionine.

Another preferred treatment regimen employs dl-methionine in the dosage range of 0.5 grams to 3 grams per day and the analgesic acetaminophen in the amount of 325 mg per 0.5 gram of methionine.

Another preferred treatment regimen employs dl-methionine in the dosage range of 0.5 grams to 3 grams per day and the analgesic ibuprofen in the amount of 300 mg per 0.5 gram of methionine.

Typically, persons suffering injury, physical or surgical, or from burns or other sources, have pain associated with that injury because of the inflammation resulting from immigration of lymphocytes. This inflammation is reduced when the individual consumes the dl or d-form of the methionine compound, preferably 1.5 to 3 grams per day. If the injury is major rather than minor, the dl-mixture is preferred because the l-form aids in tissue regeneration. In more severe injuries, the methionine dosage form may include a unit dosage of analgesic as defined above to further reduce the pain effects of the injury.

For treating pain in an animal, except for primates, the methionine compound is preferably administered as an N-acyl derivative in a species dependent daily dosage ranging from about 10 to 100 mg/kg/day until the pain is relieved.

For animal treatment, N-blocked dl-methionine can be used to get the benefit of improved healing as well as reduced inflammation. Animal treatments can also be improved by combining the N-blocked methionine forms with analgesics.

Inflammatory Joint Pain

In another preferred embodiment, using the methods shown above for Inflammatory Pain, joint pain in a subject may be treated with methionine compounds as defined above. Typically, a person experiencing joint pain consumes about 1.0 to 3.0 grams of dl-methionine in equal spaced daily doses for relief from the pain. Return of the joint pain usually follows cessation of methionine intake.

For treating joint pain in an animal, the methionine compound is administered as an N-acyl compound in a species dependent daily dosage until the inflammation is relieved. For dogs, horses, or other animals that normally utilize d-methionine, treatment in the diet with N-acetyl-d-methionine is preferred, preferably at a daily dosage of about 10 to 100 mg/kg/day for a period of 15 days.

Wound Healing

In another preferred embodiment, the method employs a composition to improve wound healing at an inflamed wound site of a subject. The subject is administered in dosage form an effective anti-inflammatory amount of at least one methionine compound as defined above. To prevent elevated homocysteine levels glycine or serine is given with methionine. As a by-product of reduced inflammation and as an independent benefit, less scarring (fibrosis) occurs during healing. Typically, persons consuming 1 to 3 grams per day when recovering from surgical wounds show reduced scarring. Based on the benefit for wound healing, a similar benefit for burn healing should result from the treatment regimen with methionine, as described herein for wound healing.

For promoting wound healing in an animal, the methionine compound is administered in non-primates preferably in the d-form as an N-acyl derivative, preferably in the diet, in a species dependent daily dosage ranging from about 10 to 100 mg/kg/day until inflammation at the wound site is relieved. For animal treatment, the N-blocked dl-methionine is used preferably to get the benefit of improved healing (the l-form component) and reduced inflammation (the d-form component).

Athletic Pain

In another preferred embodiment, using the methods shown above for Inflammatory Pain, athletic pain in a human subject may be treated using methionine compounds as defined above. Athletes taking 1.0 grams of dl-methionine three times per day with meals and exercising vigorously three times per week typically noted significant reduction in soreness due to the exercise regimen. The athletes also noted improved performance.

Recurrent Headache Pain

In another preferred embodiment, using the methods and shown above for Inflammatory Pain, the symptoms of recurrent headache, such as migraine and cluster headache, may be prevented by using an effective headache pain relieving amount of at least one methionine compound as defined ' with glycine or serine to normalize homocyste. uent or chronic use the method of the inv .. mploys at least one homocysteine affecting vitamin: B6, B12 and folate.

A preferred preventative treatment regimen is a daily oral dose, preferably at least one gram total in 2 to 3 spaced doses, of dl-methionine. Migraine headache typically is reduced in frequency or severity by daily comsumption of dl-methionine, with recurrence of greater frequency or severity after cessation of consumption.

In some cases a migraine attack may be prevented by administration of dl-methionine at the first signs of a migraine headache. A typical example is a case were the early signs of a migraine attack was top left quadrant prodromal head (subcrainial) tingling. Previously this was a signal for a migraine attack lasting 3-4 days. This symptom would normally preceed mirgraine attacks. The frequency of migraine attacks generally were 4 to 6 attacks over a 8 week period. After prodromal symptoms (subcranial tingling) in the morning the patient took 1.0 gram dl-methionine at lunch; then 1.0 gram åt dinner; 1.0 gram at bed time and 1.0 gram at rising in the morning. During this time the patient also took 1.0 gram of glycine at the dinner meal and 1.0 gram glycine at breakfast. No migraine occured during the following 2 week period while the patient continued to consume 0.5 gram dl-methionine twice a day with 1.0 gram glycine twice a day.

Dietary Formulations

To the extent that conditions benefited by the comsumption of dl-methionine are the result of a dietary deficiency of l-methionine it may be desirable to replenish methionine in food products as is currently done for a number of vitamins that are also made unavailable by food processing. The invention also employs methods for providing methionine in the final product for consumption in the amount that provides for replacement of unavailable methionine and additional methionine that would accomplish the teachings herein where it is desirable to obtain the additional antioxidant amount in a normal food item.

Damico (U.S. Pat. No. 3,952,115) teaches the addition of N-acyl l-methionine as a preferred method to reduced undesired effects of methionine supplementation. He teachs that the amount of methionine to be added to methionine-deficient protein can be determined by amino acid analysis in the case of proteins known to be low in methionine content such that methionine should be added up to the level characteristic for egg protein (an amount recognized by the U.S. Food and Drug administration as the upper limit for addition of methionine for commercial foods). In the case of proteins for which methionine is lost by food processing such as extracted protein of soybeam he teaches that the amount of methionine to be added for proper nutrition involves adding methionine derivatives as determined by rodent feeding experiments.

Because of the role that inflammatory cells play in long term tissue damage and because of the known dietary correlations of several serious inflammatory pain conditions that may be affected by reduced control of inflammatory cells, correction of a chronic marginal dietary deficiency of methioinine and thus improved long term control of inflammatory cells can be expected to reduce the severity or incidence of these conditions. Examples of the reduced control of inflammatory cells that may be due to a marginal dietary deficiency of available methionine for humans include joint pain, arthritis pain and migraine headaches.

A preferred embodiment employs a method for amelioriating symptoms of chronic pain conditions in a human subject in need thereof, such as joint pain, arthritis pain and recurrent headache pain, and the like, such method employing provision to the subject of foodstuff comprising essentially the food ingredient and a nutritionally adequate amount of a methionine compound as determined by human nitrogen balance studies or other methods validated thereby, selected from the group consisting of the methionine hydroxy analogs and dl-methionine compounds; and pharmaceutically acceptable N-(mono-and di/carboxylic acid) acyl derivatives of methionine and alkyl esters methionine and methionine hydroxy analogs (where n=2).

In another preferred embodiment for persons in an institutional setting the methionine portion of the foodstuff described above is provided in sufficient amounts such that the total l-methionine content in the final food product is more than 3 grams l-methionine per 100 grams protein but less than 15 grams of l-methionine compound per 100 grams protein.

PREPARATION OF PHARMACEUTICAL COMPOSITIONS

When being utilized as pharmacological agents, the compounds of the invention can be prepared and administered in a wide variety of oral dosage forms. It will be clear to those skilled in the art that the following dosage forms may comprise as the active component, one or more compounds of formula I, corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form perparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredients.

Suitable solid carriers are magnesium carbonate, magnesium stearate, talc, sugar, lactose, pectin, dextrin, starch, gelatin, tragacanth, methyl cellulose, sodium carboxymethyl celluose, a low melting point wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration. For information and details concerning tablet formulations see Remington's Pharmaceutical Sciences, Gennaro, A. Ed., 17th Edition, 1985, p. 1585–602, and incorporated herein by reference.

Liquid form preparations include solutions, suspensions, and emulsions. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing descrete quantities of preparation, for example, packeted tablets, capsules, and powders in vials or ampoules. The unit dosage form can also be a capsule, cachet, or tablet itself or it can be the appropriate number of any of these package forms.

The quantity of active compound in a unit dose of preparation may be varied or adjusted from 100 to 1000 mg. according to the particular application and the potency of the active ingredient.

In therapeutic use as pharmacological agents the compounds utilized in the pharmaceutical method of this invention are administered at the initial dosage of about 10 to about 50 mg per kilogram. A dose range of about 15 mg to about 30 mg per kilogram is preferred. The dosages, however, may be varied depending upon the severity of the condition being treated, and compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The dosage preferably is in a sustained or controlled release form (e.g. an enteric coated or slow release dosage form) to insure that the dosage is released in the intestine and a uniformly elevated blood level of the methionine compound is achieved, as described above.

The invention and the best mode of practicing the same are illustrated by the following examples of preferred embodiments of selected compounds and their preparation.

EXAMPLE 1

| CAPSULES Example 1a d-Methionine 100 mg, 250 mg or 500 mg | |
|---|---|
| d-Methionine | 500 g |
| Lactose USP, Anhydrous q.s. or | 200 g |
| Sterotex Powder HM | 5 g |

Combine the methionine and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg., 352.5 mg., or 705 mg. of the blend, respectively, for the 100 mg., 250 mg., and 500 mg. containing capsules.

| Example 1b dl-Methionine 100 mg, 250 mg or 500 mg | |
|---|---|
| dl-Methionine | 500 g |
| Lactose USP, Anhydrous q.s. or | 200 g |
| Sterotex Powder HM | 5 g |

Mix and fill as per Example 1a.

EXAMPLE 2

| TABLETS | |
|---|---|
| The Methionine Compound | 250 g |
| Corn Starch NF | 200 g |
| Cellulose, Microcrystalline | 46 g |
| Sterotex Powder HM | 4 g |
| Purified Water q.s. | 300 ml |

Combine the corn starch, the cellulose and the methionine compound together in a planetary mixer and mix for two minutes. Add the water to this combination and mix for one minute. The resulting mix is spread on trays and dried in a hot air oven at 50 degrees C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 100 mg., 500 mg., and 1000 mg. respectively, of the total mix are formed with appropriate sized punches for the 50 mg., 250 mg., or 500 mg. containing tablets.

EXAMPLE 3

| SUPPOSITORIES Example 3a d-Methionine 125 mg, 250 mg, or 500 mg per 3 G | | | |
|---|---|---|---|
| dl-Methionine | 125 mg | 250 mg | 500 mg |
| Polyethylene Glycol 1540 | 1925 mg | 1750 mg | 1400 mg |
| Polyethylene Glycol | 825 mg | 750 mg | 600 mg |

-continued

SUPPOSITORIES
Example 3a
d-Methionine
125 mg, 250 mg, or 500 mg per 3 G

8000

Melt the Polyethylene Glycol 1540 and the Polyethylene Glycol 8000 together at 60 degrees C. and dissolve dl-Methionine into the melt. Mold this total at 25 degrees C. into appropriate suppositories.

Example 3b
dl-Methionine
125 mg, 250 mg, or 500 mg per 3 G

| dl-Methionine | 125 mg | 200 mg | 500 mg |
|---|---|---|---|
| Polyethylene Glycol 1540 | 1925 mg | 1750 mg | 1400 mg |
| Polyethylene Glycol 8000 | 825 mg | 750 mg | 600 mg |

Prepare as per Example 3a above.

A preferred formulation is one where the total mix is constituted to also contain at least one member of the following group or groups: (1) glycine and serine from 1/5 to 3 times the Methionine content per tablet, (2) vitamins B12, B6, or folic acid where the total daily dosage range for each is: vitamin B12, 0.3 to 30 mcg; vitamin B6, 0.2 to 20 mg; folic acid, 40 to 4000 mcg, and combinations thereof; (3) inactive excipients, such as cellulose acetate phthalate, used to coat the product to provide insolubility in the stomach, and solubility in the intestines, (4) an oral analgesic in unit dosage amount per tablet, and (5) combinations thereof.

Having thus described our invention, what we claim and desire by Letters Patent to secure are the following.

We claim:

1. A method for treating the inflammation of joint pain in a subject in need of such treatment, comprising administration to the subject in dosage form an effective joint pain relieving amount of at least one methionine compound selected from the group consisting of a compound having the structural formula I

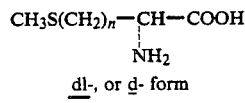

dl-, or d- form and pharmaceutically acceptable N-acyl derivatives of methionine and alkyl esters methionine, where n is the integer 2.

2. A method for treating joint pain in a human according to claim 1 where the methionine compound is administered in a daily dosage in the range from 1.0 to 10 grams per 70 kg. of body weight until the inflammation is relieved.

3. A method for treating joint pain in an animal according to claim 1 where the methionine compound is administered as an N-acyl compound in a species dependent daily dosage in the range from 5 to 100 milligrams per kg. of body weight until the inflammation is relieved.

4. A method for treating pain in a subject comprising administering to the subject in dosage form an effective pain relieving amount of at least one methionine compound selected from the group consisting of a compound having the structural formula I

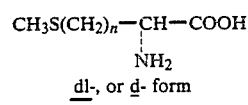

dl-, or d- form and pharmaceutically acceptable N-acyl derivatives of methionine and alkyl esters methionine, where n is the integer 2.

5. A method for treating pain in a human according to claim 4 where the methionine compound is administered in a daily dosage range from 1.0 to 10 grams per 70 kg. of body weight until the pain is relieved.

6. A method for treating pain in an animal according to claim 4 where the methionine compound is administered as an N-acyl compound in a species dependent daily dosage ranging from 5 to 100 milligrams per kg. of body weight until the pain is relieved.

7. A method according to claim 4 where the dosage form contains in addition at least one homocysteine affecting vitamin selected from the group consisting of vitamin B12, B6, or folic acid, in an amount sufficient to enable the systemic conversion of excess homocysteine present in the system to methionine and cysteine, where the total daily dosage range of vitamin B12, B6 or folic acid corresponds to: vitamin B12, 0.3 to 30 micrograms; vitamin B6, 0.2 to 20 milligrams; folic acid, 40 to 4000 micrograms; and combinations thereof.

8. A method according to claim 5 where the dosage form contains in addition one homocysteine affecting amino acid selected from the group consisting of serine and glycine, in an amount sufficient to enable the systemic conversion of excess homocysteine present in the system to cysteine, said amount ranging from 1/5 to 3 times the methionine compound.

* * * * *